United States Patent

Takemoto et al.

[11] Patent Number: 5,256,822
[45] Date of Patent: Oct. 26, 1993

[54] IMINE DERIVATIVES AND PROCESS FOR PRODUCTION THEREOF

[75] Inventors: Ichiki Takemoto, Kawanishi; Takeo Fujii, Toyonaka; Hideyuki Goto, Takatsuki; Ritsu Okajima, Ibaraki, all of Japan

[73] Assignee: Sumitomo Chemical Company, Limited, Osaka, Japan

[21] Appl. No.: 13,923

[22] Filed: Feb. 5, 1993

[30] Foreign Application Priority Data

Feb. 7, 1992 [JP] Japan ................................ 4-22479

[51] Int. Cl.$^5$ ............................ C07C 251/24
[52] U.S. Cl. ........................................ 564/276
[58] Field of Search ................................ 564/276

*Primary Examiner*—Richard L. Raymond
*Attorney, Agent, or Firm*—Birch, Stewart, Kolasch & Birch

[57] ABSTRACT

There is disclosed an imine derivative of the general formula:

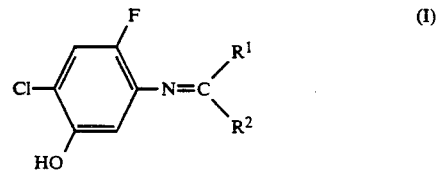

wherein $R^1$ and $R^2$ are the same or different and are hydrogen, $C_1$–$C_6$ alkyl or aryl, with the proviso that $R^1$ and $R^2$ are not simultaneously hydrogen; or $R^1$ and $R^2$ are joined together to form $C_4$–$C_6$ alkylene. Also disclosed is a process for the production of the imine derivative.

8 Claims, No Drawings

IMINE DERIVATIVES AND PROCESS FOR PRODUCTION THEREOF

FIELD OF THE INVENTION

The present invention relates to imine derivatives which are useful as intermediates for production of various medicaments and agrochemicals. It also relates to a process for the production of the imine derivatives.

BACKGROUND OF THE INVENTION

As a conventional process of producing ether derivatives of aminophenols (2-fluoro-4-chloro-5-(1-methyl-2-propynyl)aniline is a typical example thereof), which are intermediates for production of a herbicide as described in JP-A 58-38256, there has been known a process as described in JP-A 63-310855, which requires the protection of amino groups by acylation and their deprotection. This process, however, involves complicated procedures, and therefore, it cannot always be said that this process is suitable for the production on an industrial scale. For this reason, there is a great demand for development of a more simple process of producing ether derivatives of aminophenols.

SUMMARY OF THE INVENTION

Under these circumstances, the present inventors have intensively studied a process of synthesizing ether derivatives of aminophenols. As the result, they have found novel imine derivatives as useful intermediates for production of these ether derivatives, as well as their production process, thereby completing the present invention.

That is, the present invention provides novel imine derivatives of the general formula:

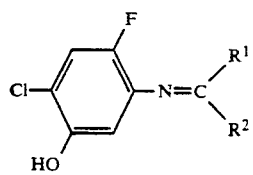

wherein $R^1$ and $R^2$ are the same or different and are hydrogen, $C_1$–$C_6$ alkyl or aryl, with the proviso that $R^1$ and $R^2$ are not simultaneously hydrogen; or $R^1$ and $R^2$ are joined together to form $C_4$–$C_6$ alkylene.

Also provided is a process for the production of the imine derivatives, comprising the step of reacting 5-amino-2-chloro-4-fluorophenol with an appropriate carbonyl compound of the general formula:

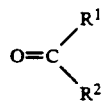

wherein $R^1$ and $R^2$ are the same as defined above.

DETAILED DESCRIPTION OF THE INVENTION

The imine derivative (I) of the present invention can be produced by reacting 5-amino-2-chloro-4-fluorophenol with the carbonyl compound (II). The substituents $R^1$ and $R^2$ of the carbonyl compound (II) as the raw material used in this reaction may be the same or different and are hydrogen; $C_1$–$C_6$ alkyl such as methyl, ethyl, n-propyl, i-propyl, n-butyl, i-butyl, sec-butyl, t-butyl, n-amyl, i-amyl, secamyl, t-amyl, neopentyl or n-hexyl; or aryl such as phenyl or naphthyl, which may be optionally substituted with $C_1$–$C_3$ alkyl, halogen, nitro or phenyl. The substituents $R_1$ and $R_2$ may also be joined together to form $C_4$–$C_6$ alkylene such as tetramethylene, pentamethylene or hexamethylene.

Typical examples of the carbonyl compound of the general formula (II) are aliphatic aldehydes such as propionaldehyde and butyraldehyde; aliphatic ketones such as methyl ethyl ketone, methyl isobutyl ketone, diethyl ketone and dibutyl ketone; aromatic aldehydes such as benzaldehyde; aromatic ketones such as acetophenone and propiophenone; and alicyclic ketones such as cyclopentanone and cyclohexanone.

The above reaction is usually carried out in a solvent. Examples of the solvent are aromatic compounds such as benzene, toluene and xylene; halogenated aromatic compounds such as monochlorobenzene; halogenated hydrocarbon compounds such as methylene chloride and dichloroethane; aliphatic hydrocarbon compounds such as hexane and heptane. These solvents may be used solely or in any combination with each other. The amount of solvent to be used is not particularly limited. Alternatively, the carbonyl compound as the raw material may also be used to serve as a solvent or in admixture with any solvent as described above.

The amount of carbonyl compound to be used is one mole or more, per mole of 5-amino-2-chloro-4-fluorophenol. In cases where the carbonyl compound is used both as the raw material and as the solvent, it may be used at great excess amounts.

The reaction temperature is usually in the range of from room temperature to the boiling point of the solvent used.

The reaction may be carried out with the use of an acid catalyst such as sulfuric acid, hydrochloric acid, acetic acid, propionic acid, haloaceric acid, p-toluenesulfonic acid or methanesulfonic acid. The catalyst, if required, is used usually at catalytic amounts for 5-amino-2-chloro-4-fluorophenol.

In the reaction, water formed as a by-product can be removed by distillation, or by allowing a dehydrating agent such as molecular sieve or calcium chloride, to exist in the reaction system or to come in contact with the solvent under reflux.

The above reaction makes possible the production of an imine derivative (I) with high efficiency.

Typical examples of the imine derivative (I) thus obtained are 5-(1,3-dimethylbutylidenamino)-2-chloro-4-fluorophenol, 5-(benzylidenamino)-2-chloro-4-fluorophenol, 5-(1-methylpropylidenamino)-2-chloro-4-fluorophenol, 5-(1-ethylpropylidenamino)-2-chloro-4-fluorophenol, 5-(1-methylbenzylidenamino)-2-chloro-4-fluorophenol, 5-(1-propylidenamino)-2-chloro-4-fluorophenol and 5-(cyclohexylidenamino)-2-chloro-4-fluorophenol. These imine derivatives can be used as intermediates for production of various medicaments and agrochemicals; for example, 5-(1,3-dimethylbutylidenamino)-2-chloro-4-fluorophenol can be converted into a known herbicide as follows:

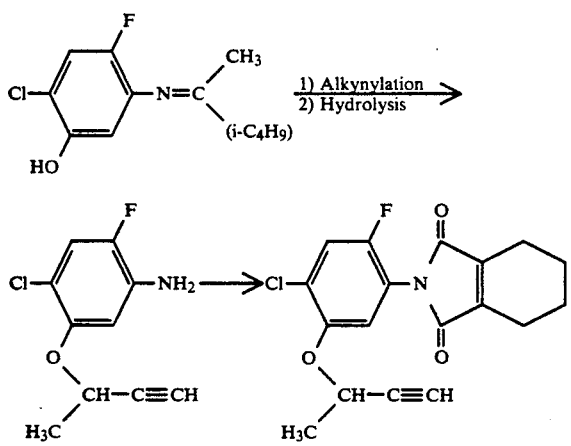

According to the present invention, imine derivatives (I) can be obtained with simple procedures and high yield, which is advantageous for the production on an industrial scale. The imine derivatives (I) thus obtained are useful as intermediates for production of various medicaments and agrochemicals.

The present invention will be further illustrated by way of the following examples which are not to be construed to limit the scope thereof.

EXAMPLE 1

Synthesis of 5-(1,3-dimethylbutylidenamino)-2-chloro-4-fluorophenol

A 50-ml four-neck flask equipped with a Vigreux column (2 cm$\phi$×25 cm) and a dehydrating column (filled with molecular sieve) attached thereon was charged with 5-amino-2-chloro-4-fluorophenol (1 g), methyl isobutyl ketone and heptane (weight ratio, 4:1; 40 g), and p-toluenesulfonic acid (4 mg). The mixture was dehydrated under reflux at 60° C. under reduced pressure (constant at 150 mmHg) for 6 hours. The concentration under reduced pressure gave 1.5 g of 5-(1,3-dimethylbutylidenamino)-2-chloro-4-fluorophenol (yield, 100%), m.p., 92°–97° C.; MS (m/z): 243 (M+) 228, 186; NMR (CDCl$_3$, $\delta$) as a 1:4 mixture of cis and trans forms: 0.80 and 1.00 (d, 6H, J=6 Hz), 1.80 and 2.20 (s, 3H), 2.0–2.2 and 2.35–2.38 (m, 3H), 6.3 and 6.4 (d, 1H, J=7.6 Hz), 6.6–7.0 (broad, 1H), 7.04 (d, 1H, J=9.6 Hz).

EXAMPLE 2

Synthesis of 5-benzylidenamino-2-chloro-4-fluorophenol

A 50-ml four-neck flask equipped with a dehydrating column was charged with 5-amino-2-chloro-4-fluorophenol (1 g), benzaldehyde (0.68 g), p-toluenesulfonic acid (10 mg) and toluene (50 g). The mixture was dehydrated under reflux under normal pressure for 5 hours, and then concentrated under reduced pressure. The precipitated crystals were filtered and washed with a small amount of hexane to give 1.46 g of 5-benzylidenamino-2-chloro-4-fluorophenol as pale brown needle crystals (yield, 94.5%), m.p., 157°–159° C.; MS (m/z) 249 (M+) 172; NMR (CDCl$_3$, $\delta$): 5.1–5.8 (broad, 1H), 6.83 (d, 1H, J=7.6 Hz), 7.15 (d, 1H, J=9.6 Hz), 7.4–7.6 (m, 3H), 7.8–8.0 (m, 2H), 8.47 (s, 1H).

EXAMPLE 3

Another synthesis of 5-(1,3-dimethylbutylidenamino)-2-chloro-4-fluorophenol

A 50-ml four-neck flask equipped with a Vigreux column (2 cm$\phi$×25 cm) and a dehydrating column attached thereon was charged with 5-amino-2-chloro-4-fluorophenol (1.62 g), methyl isobutyl ketone (32.4 g) and concentrated sulfuric acid (50 mg). The mixture was dehydrated under reflux at 100° C. under reduced pressure (constant at 500 mmHg) for 7 hours. The concentration under reduced pressure gave 2.4 g of 5-(1,3-dimethylbutylidenamino)-2-chloro-4-fluorophenol (yield, 98%). It was found that the mass spectrum and NMR spectrum of the compound thus obtained correspond to those of the compound obtained in Example 1.

EXAMPLES 4 TO 8

Various imine derivatives as shown in Table 1 can be obtained in the same manner as described in Example 2, except that methyl ethyl ketone (Example 4), ethyl propyl ketone (Example 5), acetophenone (Example 6), propionaldehyde (Example 7) or cyclohexanone (Example 8) is used in place of benzaldehyde.

TABLE 1

| Example No. | R$^1$ | R$^2$ |
|---|---|---|
| 4 | CH$_3$ | C$_2$H$_5$ |
| 5 | C$_2$H$_5$ | n-C$_3$H$_7$ |
| 6 | CH$_3$ | C$_6$H$_5$ |
| 7 | n-C$_3$H$_7$ | H |
| 8 | —(CH$_2$)$_5$— | |

What is claimed is:

1. An imine derivative of the general formula:

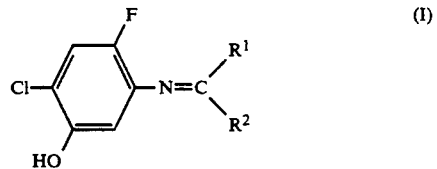

wherein R$^1$ and R$^2$ are the same or different and are hydrogen, C$_1$–C$_6$ alkyl or aryl, with the proviso that R$^1$ and R$^2$ are not simultaneously hydrogen; or R$^1$ and R$^2$ are joined together to from C$_4$–C$_6$ alkylene.

2. An imine derivative according to claim 1, wherein R$^1$ is methyl and R$^2$ is isobutyl.

3. An imine derivative according to claim 1, wherein R$^1$ is hydrogen and R$^2$ is phenyl.

4. An imine derivative according to claim 1, wherein R$^1$ is methyl and R$^2$ is ethyl.

5. An imine derivative according to claim 1, wherein R$^1$ is ethyl and R$^2$ is n-propyl.

6. An imine derivative according to claim 1, wherein R$^1$ is methyl and R$^2$ is phenyl.

7. An imine derivative according to claim 1, wherein R$^1$ is n-propyl and R$^2$ is hydrogen.

8. An imine derivative according to claim 1, wherein R$^1$ and R$^2$ are joined to form a —(CH$_2$)$_5$— alkylene.

* * * * *